United States Patent [19]

Sinha

[11] Patent Number: 5,561,066
[45] Date of Patent: Oct. 1, 1996

[54] ANALYSIS OF SUPERCRITICAL-EXTRACTED CHELATED METAL IONS FROM MIXED ORGANIC-INORGANIC SAMPLES

[75] Inventor: Mahadeva P. Sinha, Temple City, Calif.

[73] Assignee: The United States of America as represented by the Administrator of the National Aeronautics and Space Administration, Washington, D.C.

[21] Appl. No.: 433,552

[22] Filed: Apr. 20, 1995

[51] Int. Cl.[6] .................................................. G01N 33/20
[52] U.S. Cl. .................. 436/73; 436/26; 436/80; 436/81; 436/82; 436/83; 436/161; 436/173; 436/174; 436/175; 436/177; 436/178
[58] Field of Search .................... 436/73, 26, 80, 436/81, 82, 83, 173, 174, 175, 177, 178, 161

[56] References Cited

U.S. PATENT DOCUMENTS

| | | | |
|---|---|---|---|
| 4,531,056 | 7/1985 | Labowsky et al. | 250/288 |
| 4,942,296 | 7/1990 | Jones | 250/288 |
| 4,977,785 | 12/1990 | Willoughby et al. | 73/863 |
| 5,190,882 | 3/1993 | Schulz et al. | 436/139 |
| 5,205,987 | 4/1993 | Ashraf-Khorassani et al. | 422/83 |
| 5,244,634 | 9/1993 | Kingston, Jr. et al. | 422/68.1 |
| 5,271,903 | 12/1993 | Durst et al. | 422/101 |
| 5,356,538 | 10/1994 | Wai et al. | 210/634 |

OTHER PUBLICATIONS

M.L. Riekkola *Amn. Acad. Sci. Fenn.*, Ser. A2 1983, 199, 55 pages.
C.M. Wai et al. *Natl. Meet.–Am. Chem. Soc., Div. Environ. Chem.* 1993, 33, 363–366.
A. Yazdi et al. *Mater. Res. Soc. Symp. Proc.* 1994, 344, 211–216.
S.A. Liebman et al. *ASTM Spec. Tech. Publ.* 1994, STP 1221, 33–37.
G. Drasch et al. *Fresenius Z Anal. Chem.* 1982, 311, 571–577.
M.L. Riekkola *Chem. Abstr.* 1983, 99, 168545z.
B. Wenclawiak et al. *Fresenius Z. Anal. Chem.* 1984, 319, 305.
M.P. Sinha et al. *Anal. Chem.* 1985, 57, 1880–1883.
M. Ashraf–Khovassani et al. *Anal. Chem.* 1987, 59, 2077–2081.
C.M. Wai et al. *Chem. Abstr.* 1993, 119, 84756n.
M.P. Sinha et al. *Anal. Chem.* 1991, 63, 2012–2016.
M.B. Shabani et al. Anal. Chem. 1991, 63, 2099–2105.
K.L. Laintz et al. *Anal. Chem.* 1992, 64, 2875–2878.
Y. Lin et al. *Anal. Chem.* 1993, 65, 2549–2551.
C.M. Wai et al. *Talanta* 1993, 40, 1325–1330.
J. Wang et al. *Anal. Chem.* 1994, 66, 1658–1663.
Y. Lin et al. *Anal. Chem.* 1994, 66, 1971–1975.
A. Yazdi *Chem. Abstr.* 1995, 122, 85902f.
S.A. Liebman et al. *Chem. Abstr.* 1995, 122, 212892e.

*Primary Examiner*—Arlen Soderquist
*Attorney, Agent, or Firm*—John H. Kusmiss

[57] ABSTRACT

Organic and inorganic contaminants of an environmental sample are analyzed by the same GC-MS instrument by adding an oxidizing agent to the sample to oxidize metal or metal compounds to form metal ions. The metal ions are converted to chelate complexes and the chelate complexes are extracted into a supercritical fluid such as $CO_2$. The metal chelate extract after flowing through a restrictor tube is directly injected into the ionization chamber of a mass spectrometer, preferably containing a refractory metal filament such as rhenium to fragment the complex to release metal ions which are detected. This provides a fast, economical method for the analysis of metal contaminants in a sample and can be automated. An organic extract of the sample in conventional or supercritical fluid solvents can be detected in the same mass spectrometer, preferably after separation in a supercritical fluid chromatograph.

17 Claims, 1 Drawing Sheet

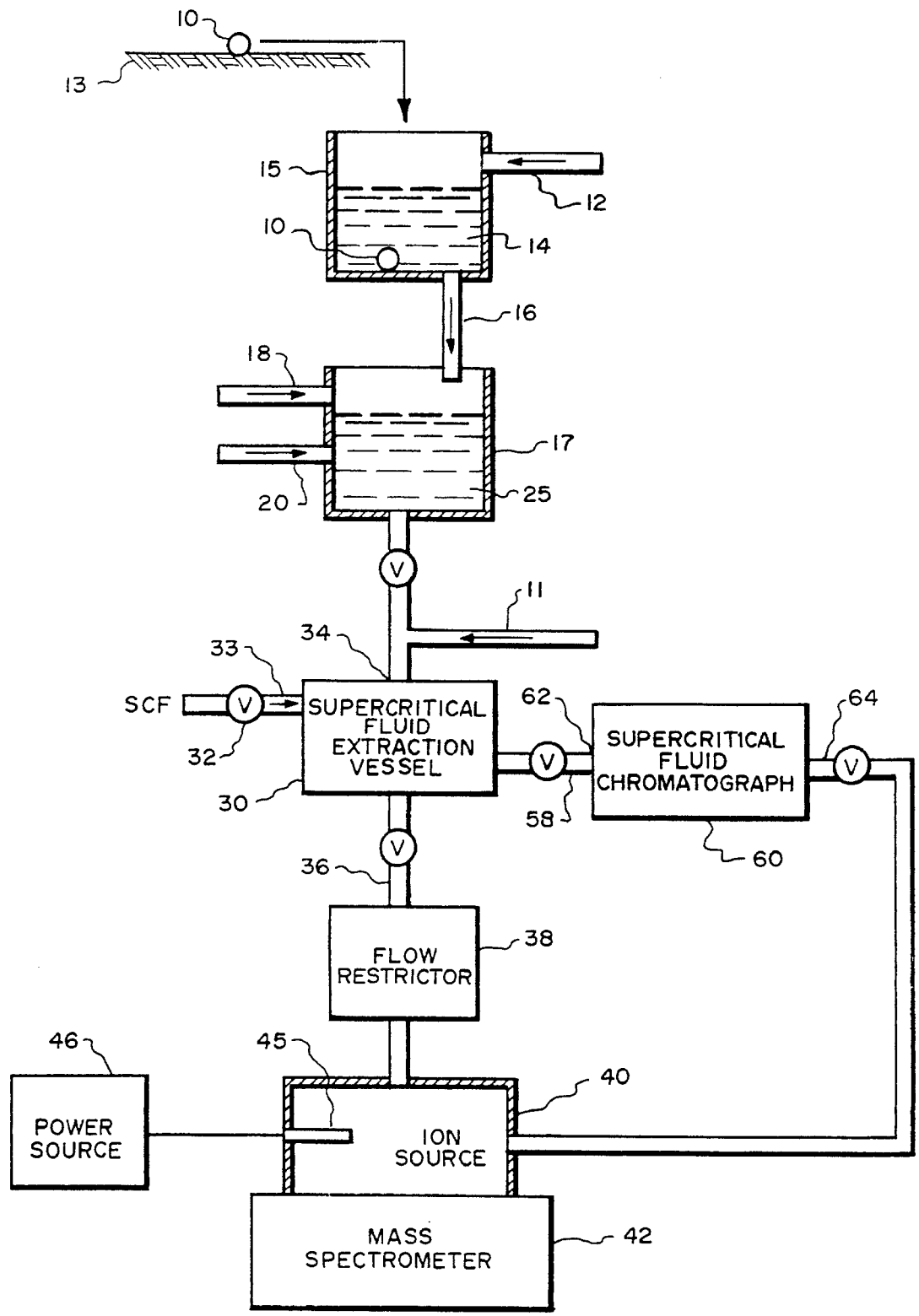

ANALYSIS OF SUPERCRITICAL-EXTRACTED CHELATED METAL IONS FROM MIXED ORGANIC-INORGANIC SAMPLES

ORIGIN OF THE INVENTION

The invention described herein was made in the performance of work under a NASA contract, and is subject to the provisions of Public Law 96-517 (35 USC 202) in which the Contractor has elected not to retain title.

TECHNICAL FIELD

The present invention relates to analysis of organic and inorganic contaminants present in environmental samples and, more particularly this invention relates to chelation of metal ions and extraction of the metal organochelate with a supercritical fluid (SCF) and on-site analysis of both organic contaminant extract and the metal chelate SCF extract in the same portable mass spectrometer.

BACKGROUND OF THE INVENTION

The long time use of landfills, dumps, ponds and other bodies of water to dispose of waste has resulted in creation of many sites containing water, soil or sediment polluted with a mixture of organic and inorganic compounds, some of which are toxic. Many of these sites are not charted or mapped. When the site containing buried waste is redeveloped, the contaminated soil is uncovered and the waste can seep into the overlying buildings and endanger the inhabitants. There is a major effort to remediate and clean all contaminated sites throughout the world and especially in the United States of America. Many times contamination is uncovered while property is being sold or during construction. It is necessary to identify the extent and type of toxic compounds present in the zone and in order to assess the type of remediation needed and to remediate the soil as soon as possible so that the sale can close or construction can proceed.

Mass spectrometry (MS) or gas chromatography-mass spectrometry (GC-MS) is one of the most sensitive and accurate means of organic analysis. It is widely used for the analysis of the organic content of environmental samples. However, it is not applicable to the detection and quantification of metals or metal ions in these samples because of the problem of extracting metals from the samples and presenting them to the mass spectrometer in vapor form.

In order to determine the metal content of an environmental sample, metals were extracted from the sample by elaborate methods and the extracted samples were analyzed by a separate analytical method using a separate instrument.

Acquisition of data would be significantly expedited if environmental samples could be analyzed on site. A field portable GC-MS system has been developed for this purpose. However, as discussed above, the GC-MS instrument can only analyze organic contaminants. If the environmental samples contain toxic metals or are suspected to contain these metals, the sample must be returned to the laboratory for elaborate extraction and analysis or a separate instrument had to be brought to the field and the elaborate inorganic extraction practiced on-site.

It would be much more convenient, and cost effective if both metals and organic compounds could be analyzed on site or at the lab in the same, GC-MS system.

STATEMENT OF THE INVENTION

In the invention, metal ions in an environmental sample are directly dissolved to form an extract. The extract is presented in vapor form to the mass spectrometer for analysis. This enables the direct application of mass spectrometry for the detection and quantification of the metals contained in various matrices in environmental samples without any extensive preparation of the sample. The same mass spectrometer instrument can now be used for the analysis of both the metal and organic contaminants in an environmental sample.

On-site analysis of the environmental samples for both metal and organic content is now possible with the use of a portable GC-MS instrument. The extraction technique is simple and the metal containing extract is converted to vapor form. Analysis of contaminated soils or other matrices can be performed in a much simpler, expeditious manner. The cost savings are substantial.

In the invention, the metals in the sample are first converted to ion form, if necessary, by reaction with an oxidizing agent such as a peroxide, suitably hydrogen peroxide or a strong mineral acid such as nitric or sulfuric acid. The metal ions could then be converted to vapor form by supercritical fluid extraction (SFE). However, most inorganic compounds have low solubility in supercritical fluids and can not be extracted nor readily analyzed as a supercritical fluid extract.

However, the metal ion compounds are solubilized in accordance with the invention by first complexing the metal ions with an organic ligand. The solubilities of the metal ion contaminants in the environmental sample in supercritical fluid solvent are greatly increased by chelation. The metal organic chelate is then extracted by a supercritical fluid. The process also brings the metal chelates into a gas phase and can be directly analyzed by SFE-MS. If one wants to separate the chelates of different metals before analysis, supercritical fluid chromatography (SFE-GC-MS) may be used to separate the mixture of metal chelates into an eluate in which the metal chelates are individually presented to the MS detector for mass spectral analysis.

In order to further increase the solubility of the metal complexes in the supercritical fluid extract, a tetraalkyl ammonium ion can be added to the chelate complex to suppress ionization of the metal ion from the metal ion-ligand complex.

The supercritical fluid extract can be directly introduced into the ion source of the MS by a flow restrictor. A heated refractory metal filament such as a Re filament in the ion source can be included to increase fragmentation of the metal ion chelates on impaction so that free metal ions are subjected to mass spectral analysis.

The on-site portable GC-MS instrument can also be utilized to analyze the organic contaminants present in the soil. A fresh sample of soil or the sample used to extract the metal content can be extracted with organic solvent and the solvent extract can be analyzed in the mass spectrometer, preferably after separation in a gas chromatograph (GC), or a supercritical fluid gas chromatograph (SFE-GC). It is preferred to first extract organic compounds from the sample to avoid degradation by reaction with the oxidizing agents. Furthermore, extraction into a supercritical fluid solvent is preferred since it is more expeditious and efficient.

Thus, the invention provides on-site analysis of both inorganic metal and organic contaminants of soil in the same instrument.

These and many other features and attendant advantages of the invention will become apparent as the invention becomes better understood by reference to the following detailed description when considered in conjunction with the accompanying drawings.

BRIEF DESCRIPTION OF THE DRAWINGS

The Figure is a schematic view of a system for the combined metal and organic analysis of an environmental sample.

DETAILED DESCRIPTION OF THE INVENTION

Referring now to the Figure, the invention proceeds by removing a sample 10 from a zone 13 suspected of being contaminated. The sample may be solid or liquid. It can be water, a body fluid, biological waste, pharmaceutical waste, petroleum waste product, or soil or sediment suspected of being contaminated with organic and inorganic compounds.

The sample 10 is then extracted for metal contaminants by first converting the metals or low soluble metal compounds such as metal oxides into metal ions dissolved in aqueous media. A strong oxidizing agent 12 is added to the sample 10 in a vessel 15 to form an aqueous suspension or solution 14 of the sample. The oxidizing agent can be a peroxide or strong mineral acid such as hydrogen peroxide, nitric acid, sulfuric acid or aqua regia to oxidize the metals or metal oxides present into metal ions. The sample may contain toxic metals such as cadmium, chromium, mercury or lead. The aqueous extract 16 containing metal ions is reacted in vessel 17 with ligands 18.

The metal ions are rendered more soluble in supercritical fluid by being complexed with at least one organic ligand 18 to form a metal chelate $ML^+$, which is soluble in a supercritical fluid. The organic complexing agent is a compound containing a plurality of complexing groups such as carbonyl or amino that surround and bind the metal ions. Representative chelating agents are ethylene diamine tetraacetic acid (EDTA), acetyl acetone, dialkyl dithiocarbamates and 8-hydroxy quinoline. A table showing formation constants (Log $K_f$) values for different metal chelates follows.

TABLE I

| | Log $K_f$ for different metal chelates. | | |
|---|---|---|---|
| Metal Ion | Acetyl Acetone | EDTA | 8-hydroxy quinoline |
| $Cd^{2+}$ | 3.8 | 16.5 | 7.8 |
| $Co^{2+}$ | 5.4 | 16.3 | 9.1 |
| $Cu^{2+}$ | 8.2 | 18.8 | 12.2 |
| $Ni^{2+}$ | 5.9 | 18.6 | 9.9 |
| $Zn^{2+}$ | 5.0 | — | 8.5 |
| $Hg^{2+}$ | — | 21.8 | — |
| $Pb^{2+}$ | — | 18.0 | 9.0 |
| $Cr^{3+}$ | — | Very favorable* | — |

*P. J. Cherney, B. Crafts, M. Hagermoser, A. Boule, R. Harbin, and B. Zak. Anal. Chem. 26, 180b, 1957.

The affinity of organic chelating agents with metal ions has been previously reported. EDTA is a commonly used ligand and possesses a high formation constant ($K_f$) with a large number of metals over a wide pH range. By choosing a mixture of ligands it may be possible to provide sequential elution of the complexed ions from a liquid or gas chromatographic column. The tendency of the complexes to dissociate can be suppressed by adding a quaternary amine 20 such as tetramethyl ammonium chloride at a concentration of at least 0.1 molar based on metal to the solution 25 of complexed metal ions.

The inorganic extract has been complexed with ligands that are supercritical-fluid-philic so as to be soluble in the SCF. The complex is dissolved in a supercritical fluid such as carbon dioxide, ammonia or nitrous oxide. Carbon dioxide is preferred since it is non-toxic and non-hazardous and can be safely vented to the atmosphere. A modifier such as MeOH can be added to the supercritical fluid. The complex is dissolved in the supercritical fluid to form a supercritical fluid extract (SFE). The supercritical fluid both dissolves and gasifies the metal ion-ligand complex.

The solution 25 of metal chelates is extracted into a supercritical fluid in a supercritical fluid extraction vessel 30. A supercritical fluid such as carbon dioxide is introduced into the vessel 30 through line 33. The solution 25 is introduced into an inlet 34 to the vessel 30. The metal chelates dissolve in the supercritical fluid to form a supercritical fluid extract (SFE) which leaves the vessel through outlet 36.

The metal ion containing extract can be analyzed directly by flowing the extract through a flow restrictor 38 into an ion source 40 of a detector 42. A mass spectrometer 42 is most preferred for the detection of the metals due to its sensitivity and general applicability. Mass spectrometer is widely used for the determination of organic compounds in an environmental sample.

In order to increase the sensitivity of detection, the metal chelate can be fragmented on a heated metal filament 45 in the ion source 40 of the MS detector 42. A refractory metal filament 45 such as a rhenium filament can be placed in the ion source 40. When the filament 45 is heated resistively by a power source 46, the metal chelates fragment and the metal ions separate from the ligands. The metal ions are detected by their mass spectral response in the detector 42.

For field analysis, the mass spectrometer is housed in a portable GC-MS unit. The gas chromatograph is preferably a supercritical fluid gas chromatograph. The metal ion extract in supercritcal fluid can be fed through the SCF-GC before delivery to the mass spectrometer. The organic contaminants of the soil sample can also be analyzed in the same portable unit.

The sample 10 can be double extracted for organic and inorganic contaminants. It is preferred to extract organic contaminants first since the strong acid or peroxide may degrade or react with the organic compounds. The organic compounds can be extracted by using supercritical fluid extraction (SFE) or by a conventional organic solvent extraction method. The first method (SFE) is preferable because of the ease of operation and automation. For solvent extraction the sample 10 can be dispersed in a conventional organic solvent such as hexane, freon or methylene chloride in the vessel 15 or the solvent can be percolated through the sample 10 in a column and a solution containing dissolved organic compounds is recovered.

An extract of the organic contaminants in supercritical fluid is prepared by placing a soil of sample 11 in the supercritical fluid vessel 30, opening the valve 32 on the line 33 and filling the vessel 30 with supercritical fluid such as carbon dioxide. The organic contaminants are extracted into the supercritical fluid to form an organic SCF extract 58.

The extract 58 is preferably interfaced to a supercritical fluid chromatograph (SFC) 60 either on-line through inlet 62 or can be collected in an off-line mode. The eluate 64 from the SFC 60 contains sequential bands of the organic contaminants. When the eluate 64 is fed to the ion source 40 of the mass spectrometer 42, the organic contaminants are ionized and sequentially detected.

Soil is analyzed by extracting a sample of the soil with a SCF to form a SCF organic extract and the soil residue extracted with an oxidizing agent to form a metal ion extract. The metal ion extract is complexed with a chelating agent to form a solution of metal chelates. The solution of metal chelates is placed in a supercritical fluid extraction vessel which can be disposed in an oven. A pump connects supply cylinders of $CO_2$ to a SCF extraction vessel.

The supercritical fluid extract of the organic contaminants can be interfaced to a supercritical fluid chromatograph (SFC). The supercritical fluid extract (SFE) of the chelated metal ions can be interfaced on-line directly to a mass spectrometer or can be collected in an off-line mode.

The extraction vessel can be disposed in an oven. A pump connects a supply cylinder of $CO_2$ or other supercritical fluid to the extraction vessel. The vessel can be stainless steel and usually has a volume from 0.5 ml to as large as 50 ml. The end-caps of the vessel are removable and usually contain removable screens or fritted metal filters and seals.

The extraction vessel is connected to a supply cylinder of solvent such as $CO_2$ by a variable flow pump. The pump provides a continuous, high pressure supply of liquid $CO_2$. A controller such as a microprocessor regulates and controls pressure in the vessel, usually to a pressure from 0 to 500 atmospheres; temperature, generally up to 150° C. and also controls flow rates and valve position and the temperature of the restrictor line. The temperature of the extraction oven is thermostatically controlled. A typical volume for the extraction vessel is 8 ml and a suitable extraction temperature is from 35°–50° C. at a pressure from 300–480 atmospheres. For a mixture of extracting fluids ($CO_2$/MeOH) the temperature may be raised higher to 130° C.

After a period of dynamic or static extraction, the inorganic extraction effluent is channeled dynamically through a restrictor. The flow through the restrictor line can be regulated by crimping a stainless steel tube, such as a 1/32 inch, 0.007 in. i.d. tube or filling the tube with fused silica. The output of the restrictor line containing the metal chelate extract is directly delivered to the same mass spectrometer used to analyze the organic extract sample.

In another mode of operation, the restrictor line is inserted directly through a septum of a capillary injection port of a GC. The supercritical fluid state is maintained until it reaches the top of the restrictor line and the supercritical fluid decompresses inside the heated injection port. The analytes remain in solution until they are within the injection port and vaporize within the port, mix with the GC carrier gas are homogenized and are flushed onto the head of the GC capillary column. The excess decompressed $CO_2$ and analytes flow out of a vent.

During SFE-GC, the solubilized analytes can exit the extraction vessel through a fused silica transfer line (10–50 um i.d.) that is inserted directly into an on-column capillary injection port. All of the solubilized analytes and decompressed gaseous $CO_2$ enter the GC capillary column. The transfer line is isolated from the GC port after the dynamic extraction mode. The temperature of the GC should be maintained above −50° C. to avoid plugging of the transfer line due to freezing of the decorepressed $CO_2$ inside the capillary column.

The organic extract can be solubilized in the same SCF extraction vessel and separated in the SCF-GC before being fed to the injection port of the ion source of the same mass spectrometer of the portable SCF-GC-MS instrument.

The analysis system of the invention allows the use of a single, portable analytical system for the on-site determination of both toxic organic and toxic metal contaminants in an environmental sample. Elaborate sample preparation is not necessary. Organic compounds can be extracted with common organic solvents or with a supercritical fluid. Inorganic metals are converted to ion form and are complexed with organic ligands to increase their solubility in supercritical fluids. The metal complexes are extracted into a supercritical fluid and can be directly analyzed in a mass spectrometer detector. Both the organic extract and supercritical fluid metal ion containing extract can be analyzed on-site by the same GC-MS or other detector instrument.

It is to be realized that only preferred embodiments of the invention have been described and that numerous substitutions, modifications and alterations are permissible without departing from the spirit and scope of the invention as defined in the following claims.

I claim:

1. A method of determining metal content of an environmental sample containing organic contamination and metal contamination comprising the steps of:

first extracting the sample to form an organic extract;

converting the metal present in the sample remaining after removing the organic extract to metal ions;

complexing the metal ions with an organic ligand to form metal ion-ligand complexes that are soluble in a supercritical fluid;

extracting the metal ion-ligand complexes with supercritical fluid to form a supercritical fluid metal containing extract;

introducing said metal containing extract into a detector;

determining the metals present in said sample introducing the organic extract into said detector; and analyzing the organic extract in said detector.

2. A method according to claim 1 in which the detector is a mass spectrometer.

3. A method according to claim 2 in which the metal containing extract is flowed through a flow restrictor before being injected into said mass spectrometer.

4. A method according to claim 1 in which the sample is first extracted in a supercritical fluid and a supercritical fluid extract containing organic contaminants is analyzed.

5. A method according to claim 4 further including the step of passing the supercritical fluid organic extract through a chromatographic column before analyzing said organic extract.

6. A method according to claim 5 in which the chromatographic column is a supercritical fluid chromatographic column.

7. A method according to claim 1 in which the metals in said sample are converted to metal ions by reaction with an oxidizing agent.

8. A method according to claim 7 in which the oxidizing agent is selected from the group consisting of peroxides and strong mineral acids.

9. A method according to claim 8 in which the ligand is selected from organic compounds containing a plurality of substituents selected from the group consisting of amino and carbonyl groups.

10. A method according to claim 9 in which the substituents are amino groups and further including the step of adding a quaternary amine to the metal-ion-ligand containing extract to reduce dissociation of the complex.

11. A method according to claim 9 in which the organic ligands are selected from the group consisting of ethylene diamine tetracetic acid, 8-hydroxy quinoline and dialkyldithiocarbamates in which the alkyl groups each contain from 1 to 8 carbon atoms.

12. A method according to claim 1 in which the supercritical fluid is selected from the group consisting of $CO_2$, ammonia and nitrous oxide.

13. A method according to claim 12 in which the supercritical fluid is $CO_2$.

14. A method according to claim 1 in which the supercritical fluid is a mixture of $CO_2$ and methanol.

15. A method of determining metal content of an environmental sample containing organic contamination and metal contamination comprising the steps of:

converting the metal present in the sample to metal ions;

complexing the metal ions with an organic ligand to form metal ion-ligand complexes that are soluble in a supercritical fluid;

extracting the metal ion-ligand with supercritical fluid to form a supercritical fluid metal containing extract;

introducing said metal containing extract directly into an ion source interfaced to a mass spectrometer detector; and determining the metals present in said sample.

16. A method according to claim 15 further including the step of fragmenting the metal-ion-organic ligand complexes in the ion source by discharging a metal filament in the ion source.

17. A method according to claim 16 in which the metal filament comprises rhenium.

* * * * *